US006981427B2

(12) United States Patent
Roggero

(10) Patent No.: US 6,981,427 B2
(45) Date of Patent: Jan. 3, 2006

(54) DEVICE FOR DISINTEGRATING BIOLOGICAL SAMPLES

(76) Inventor: Gianmarco Roggero, Via Sicilia 28, Orbassano (IT) I-10043

(*) Notice: Subject to any disclaimer, the term of this patent is extended or adjusted under 35 U.S.C. 154(b) by 0 days.

(21) Appl. No.: 10/450,002

(22) PCT Filed: Dec. 5, 2001

(86) PCT No.: PCT/EP01/14262

§ 371 (c)(1),
(2), (4) Date: Jun. 9, 2003

(87) PCT Pub. No.: WO02/048679

PCT Pub. Date: Jun. 9, 2003

(65) Prior Publication Data

US 2004/0035964 A1 Feb. 26, 2004

(30) Foreign Application Priority Data

Dec. 13, 2000 (IT) .......................... TO2000A1156

(51) Int. Cl.
*G01N 33/00* (2006.01)
(52) U.S. Cl. ..................................................... 73/866
(58) Field of Classification Search ................ 366/241, 366/242, 244, 245, 247, 249, 251–253, 150.1, 366/279, 281–283, 302, 307, 314, 315, 341, 366/197–199, 203, 401, 404; 83/401, 404, 83/416; 73/863, 806, 866
See application file for complete search history.

(56) References Cited

U.S. PATENT DOCUMENTS

| | | | | |
|---|---|---|---|---|
| 943,200 A * | 12/1909 | Peter | ........................... | 366/204 |
| 1,480,969 A | 1/1924 | Thomsom | | |
| 1,604,845 A * | 10/1926 | McKenney | .................. | 366/142 |
| 2,136,936 A * | 11/1938 | Cohen | ......................... | 366/149 |
| 4,658,711 A * | 4/1987 | Vennewald | ................... | 99/455 |
| 4,879,917 A * | 11/1989 | Eppelmann et al. | .......... | 73/866 |
| 4,891,966 A | 1/1990 | Kramer | | |
| 5,662,248 A | 9/1997 | Collard, Jr. | | |
| 5,731,199 A | 3/1998 | Roggero | | |
| 5,829,696 A | 11/1998 | DeStefano et al. | | |
| 6,257,755 B1 * | 7/2001 | Sevelle | ........................ | 366/258 |
| 6,467,662 B1 * | 10/2002 | LaRochelle | .................. | 224/310 |
| 6,508,583 B1 * | 1/2003 | Shankwitz et al. | .......... | 366/196 |
| 6,767,313 B2 * | 7/2004 | Sayce | ........................... | 482/71 |

\* cited by examiner

*Primary Examiner*—Robert Raevis

(74) *Attorney, Agent, or Firm*—Merchant & Gould P.C.

(57) ABSTRACT

A deconstituting device for the preparation of biological samples comprising: a container (2) in the form of a cup for holding the tissue to be deconstituted; a shaft (26) mounted for rotation inside the said container (2) with a blade (28) on the end inside the container; the said shaft (26) being supported axially by ball coupling means (30, 34) and having engagement means (36) on its end outside the container for coupling the said shaft to motor means; the device being used in automatic apparatus, which includes: at least one support element (54) with a plurality of housings for receiving the container; a deconstitution station (50) which includes at least one motor (52) with a drive shaft (55) for engaging the said engagement means (36) of the shaft (26) of the deconstituting device, this motor being movable between a position disengaged from the said shaft (26) and one engaging it, and; conveyor means (66, 68 and 78) for transporting the said support element (54) to the deconstitution station.

7 Claims, 6 Drawing Sheets

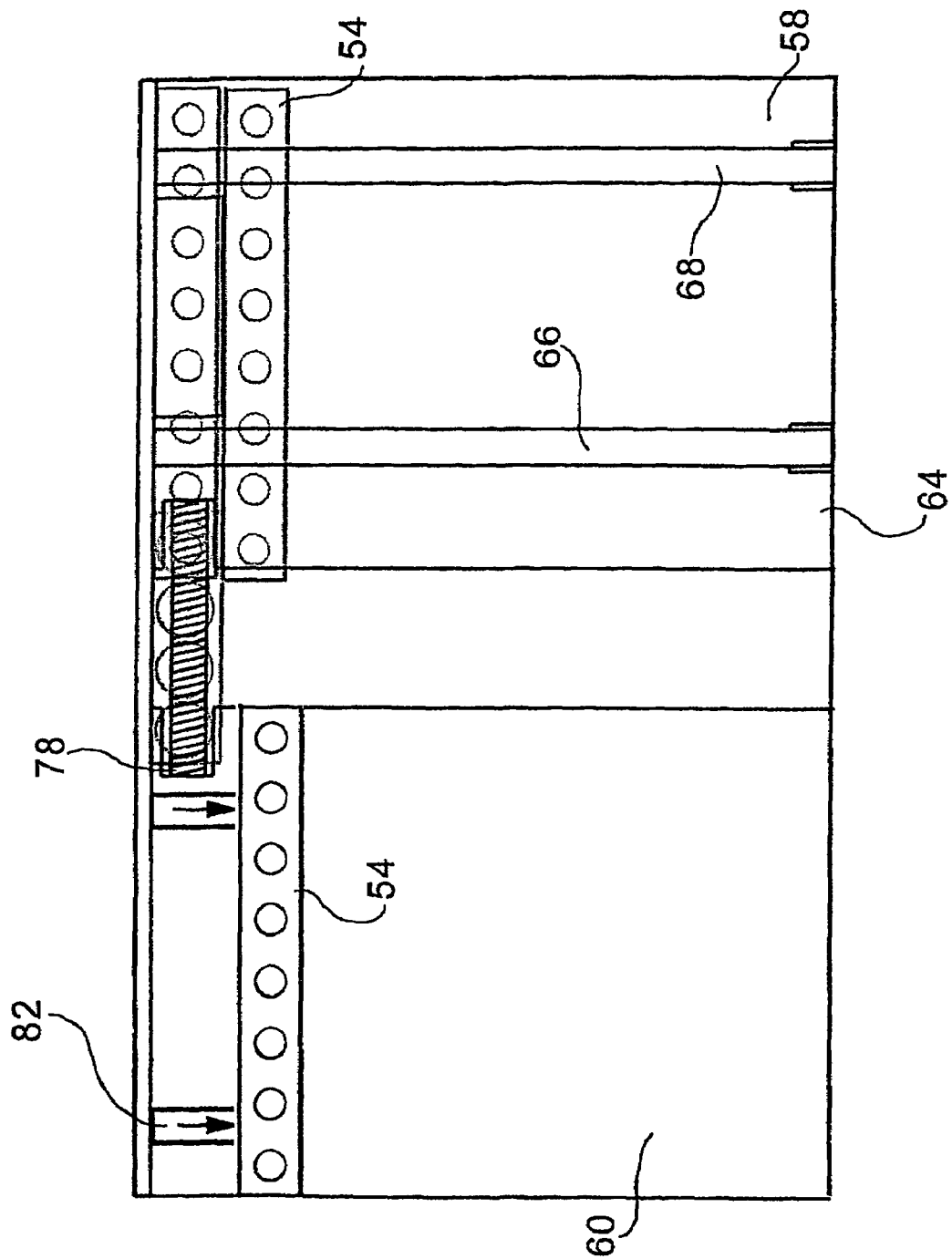

DEVICE FOR DISINTEGRATING BIOLOGICAL SAMPLES

The present invention relates to equipment for deconstituting biological samples, in particular for the preparation of homogenized samples to be tested for pathogens of Bovine Spongiform Encephalopathy (BSE)

The invention also relates to a device, preferably of a single-use, disposable type, to be used as part of this equipment.

Tests which are currently available for the diagnosis of BSE are carried out on samples of brain tissue from slaughtered animals and their purpose is to detect the presence of altered prions by means of antibodies which bond with the BSE-specific prion protein.

Correct preparation of the sample to be tested for bonding with the antibody is crucial to the success of the test. The method which is currently used requires the tissue to be deconstituted or homogenized, and then to be treated with enzymes in order to destroy any non-altered prions before the antibody is introduced to detect the presence of any abnormal prions.

The principle reason for developing the present invention was to provide automatic deconstitution/homogenization of the samples in order to reduce the time taken to prepare these samples, which severely affects the time taken to carry out testing.

An additional object of the invention was to provide equipment which ensures that homogenization is standardized and can thus be reproduced on all samples submitted for testing, while simultaneously providing an excellent level of homogenization.

In the light of these aims, the subject of the invention is deconstituting apparatus, including a specific deconstituting device, as claimed in the appended claims.

Further advantages and characteristics of the invention will become apparent from the detailed description which follows and refers to the appended drawings, provided purely by way of non-limitative example, and in which:

FIGS. 2a–2e are schematic plan views of equipment of the type shown in FIG. 1, illustrating the respective operating steps carried out by the equipment;

Figure 1:
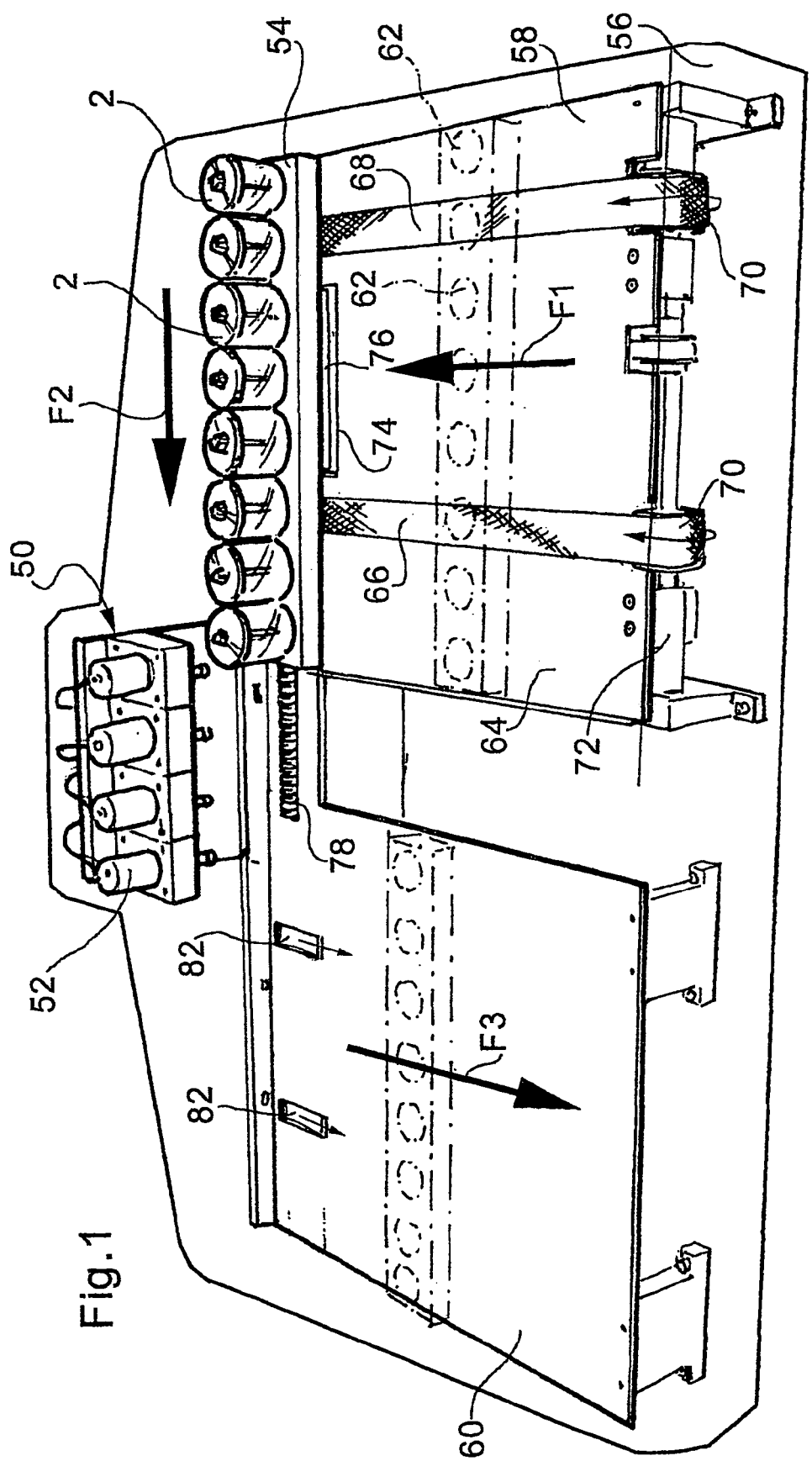
FIG. 1 is a partial perspective view of equipment according to the invention, shown without an associated casing or body in order to display the structural characteristics of the equipment.

With reference to the drawings, a deconstituting device, operable to receive and homogenize biological samples, in particular soft tissue, such as brain or marrow tissue, and produced as a low cost, disposable item for the homogenization of a single sample, is generally indicated 2.

This device includes a generally cup-shape container 4 made of a plastics material and preferably comprising an upper portion 6 with a cylindrical wall, an intermediate portion 10 with a conical wall, bottom portion 8 with a cylindrical wall and a base portion 12, preferably having a frusto-conical wall.

The container also has a lid 14 made up of three discs 16, 18 and 20, each having a central hole 22 and corresponding peripheral apertures or windows. The intermediate disc 20 is mounted for rotation between the discs 16 and 18 and has a tab 24 for rotating the intermediate disc manually so that the window thereof is aligned with those of the discs 16 and 18, making it possible to introduce the sample. One area of the intermediate disc 20 is formed by a thin membrane, of rubber for example, which can easily be pierced in order to insert a pipette for extracting the homogenized sample.

A shaft 26 is mounted for rotation inside the container and has a cutter element 28; with one or two blades for example, on the end inside the container. The shaft 26 is supported axially by the bottom of the container, by means of ball coupling means; in particular, these means include a metal ball 30, freely rotatable in a housing 32 in the bottom 12 and a spherical, or possibly frusto-conical cavity 34 in the end of the shaft 26.

The end of the shaft 26 outside the container has an engagement element 36, with a grooved surface, for example with projecting ribs for engagement with a complementary female engagement element 40, associated with a drive shaft, as described later.

Other preferred characteristics of the device 2 include the presence of ribs 42 on the inside of the bottom 12, provided to encourage the development of a vortex and, as an extra option, an annular element 44 inserted into the lower portion 8 of the container, with an optional annular formation 46 projecting into the container. The annular element 44 encourages the formation of a vortex leading towards the cutter element 28, thereby ensuring that the tissue to be homogenized is directed towards the blades.

The deconstituting device illustrated which, as stated above, constitutes a preferred embodiment, can be made of low-cost plastics materials. The ball coupling between the shaft and the bottom of the container, achieved by means of a steel ball acting as an anti-friction bearing, makes it possible to rotate the shaft very rapidly, at around 20000 rpm for example, thereby achieving total deconstitution of the tissue, with all the cells (99%) completely broken down, in a very short time, of the order of 30 seconds.

The lid 14 acts as a centering element for the shaft 26, which is freely rotatable in the hole 22.

Figure 2A:
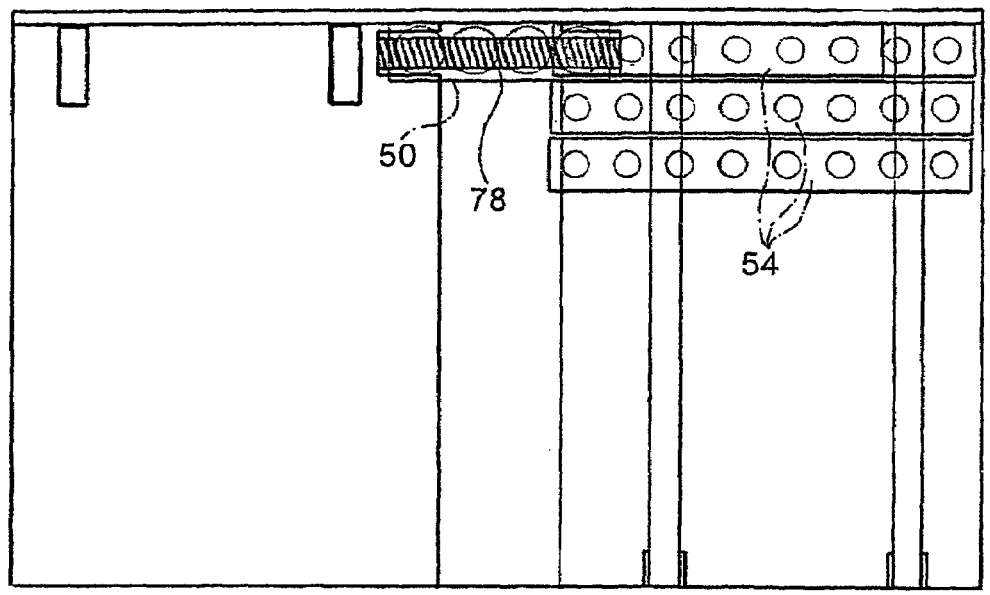
Figure 2B:
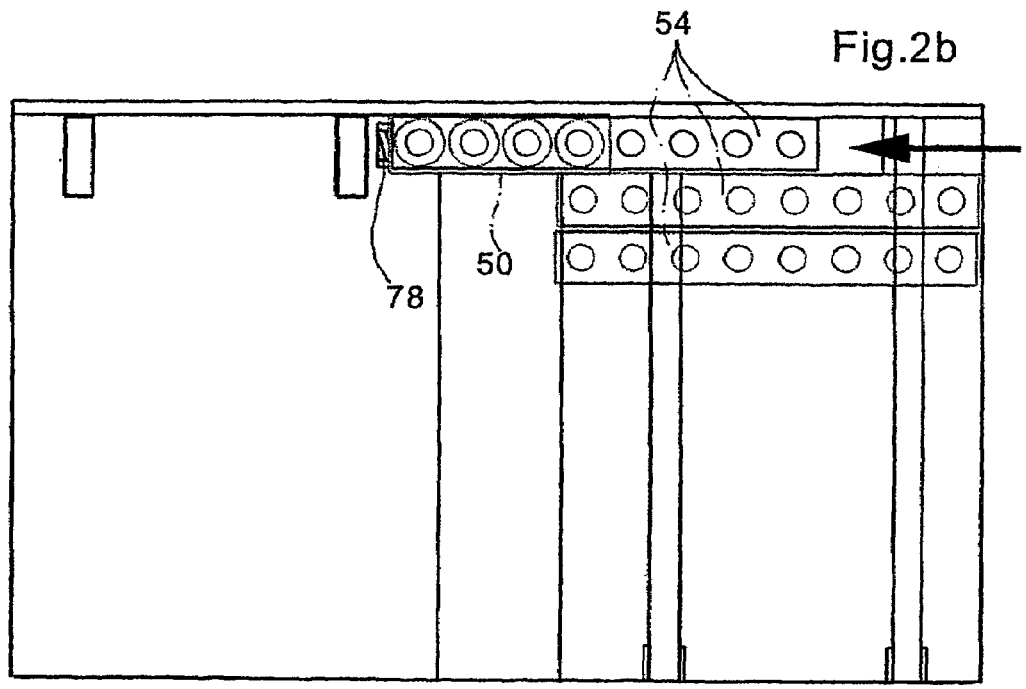
Figure 2C:
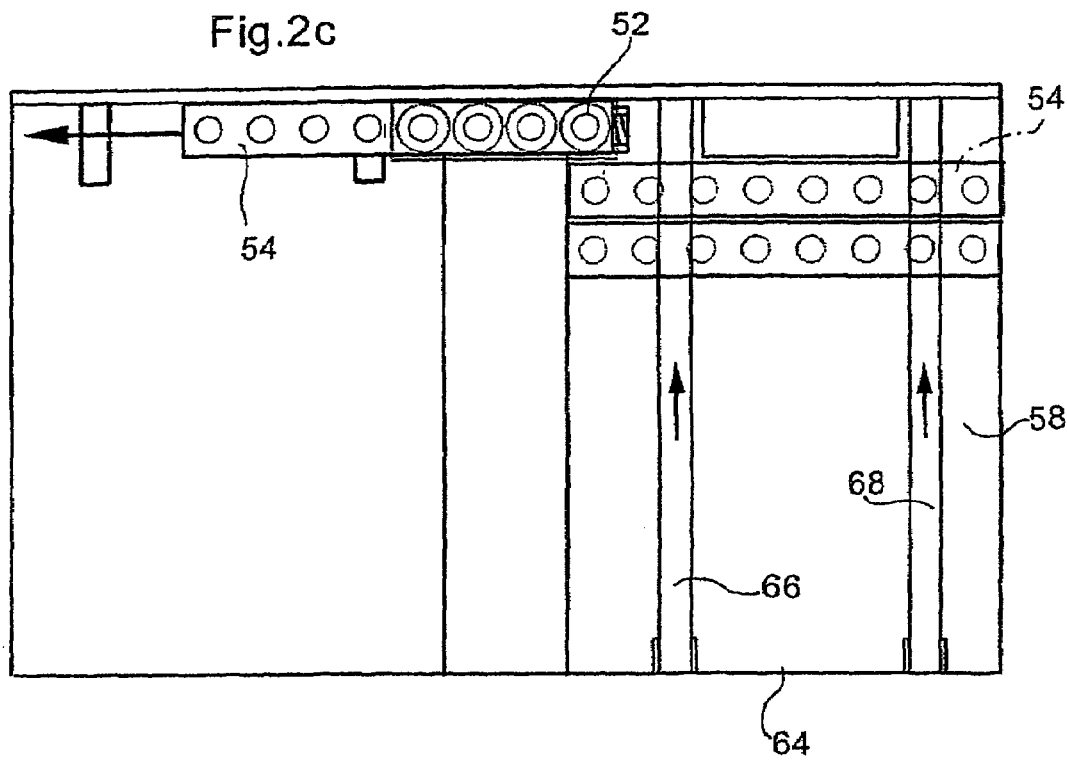
Figure 2D:
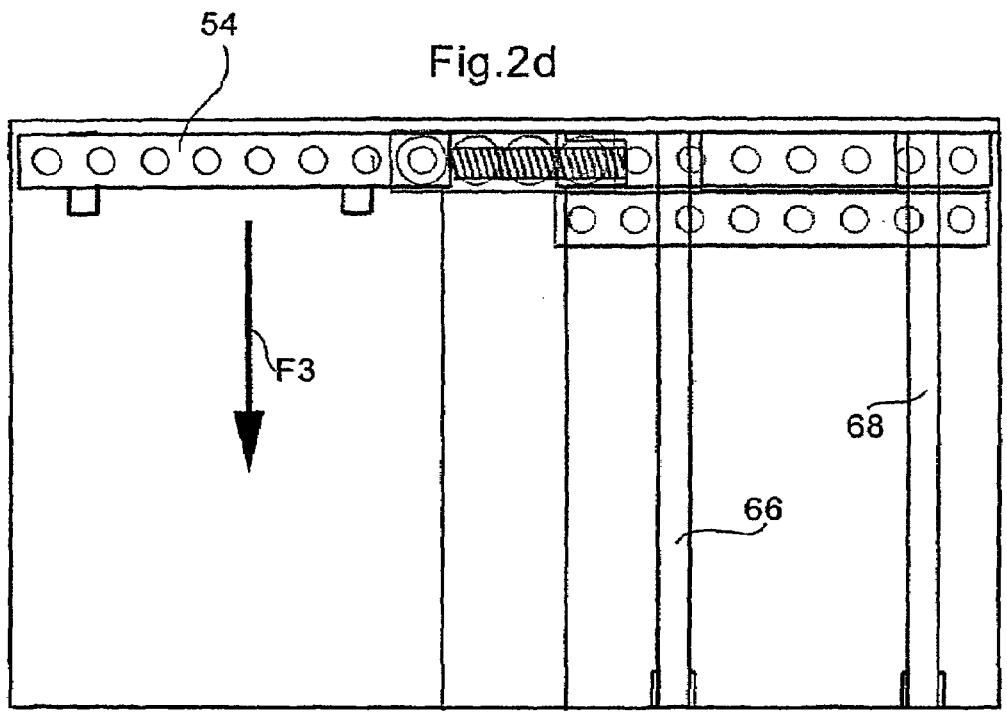
Figure 3A:
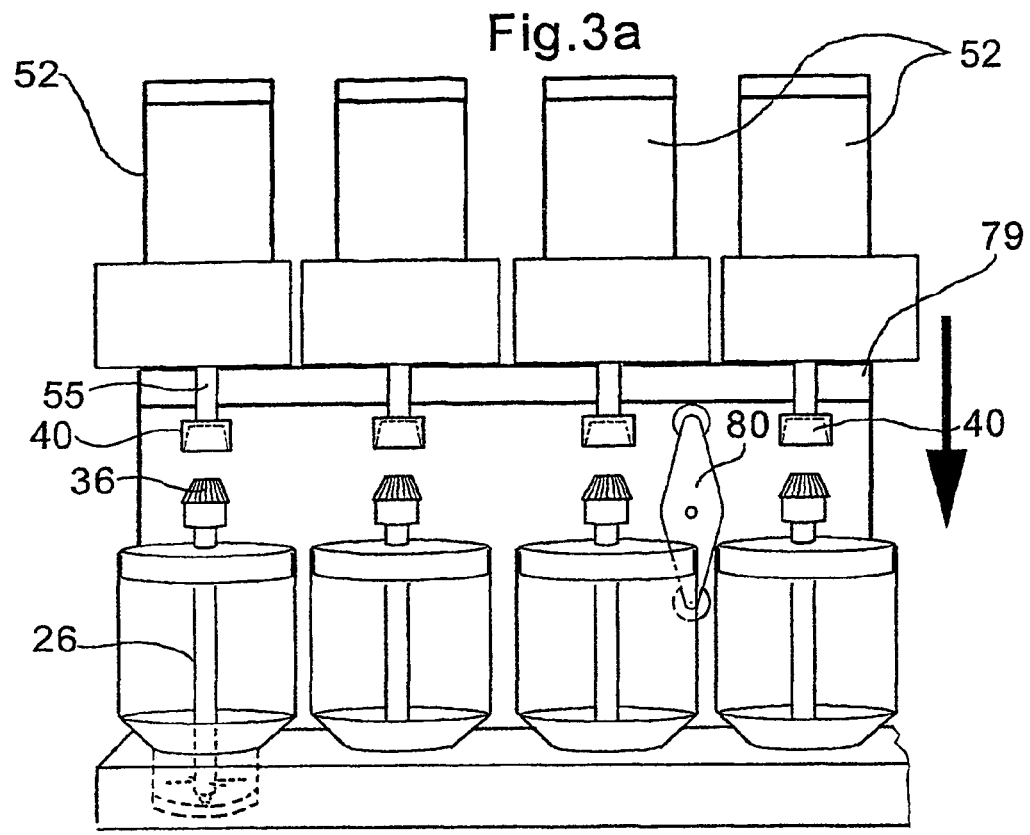
FIGS. 3a and 3b are schematic front elevations of a detail of the equipment of FIG. 1, in two successive operating stages.
Figure 3B:
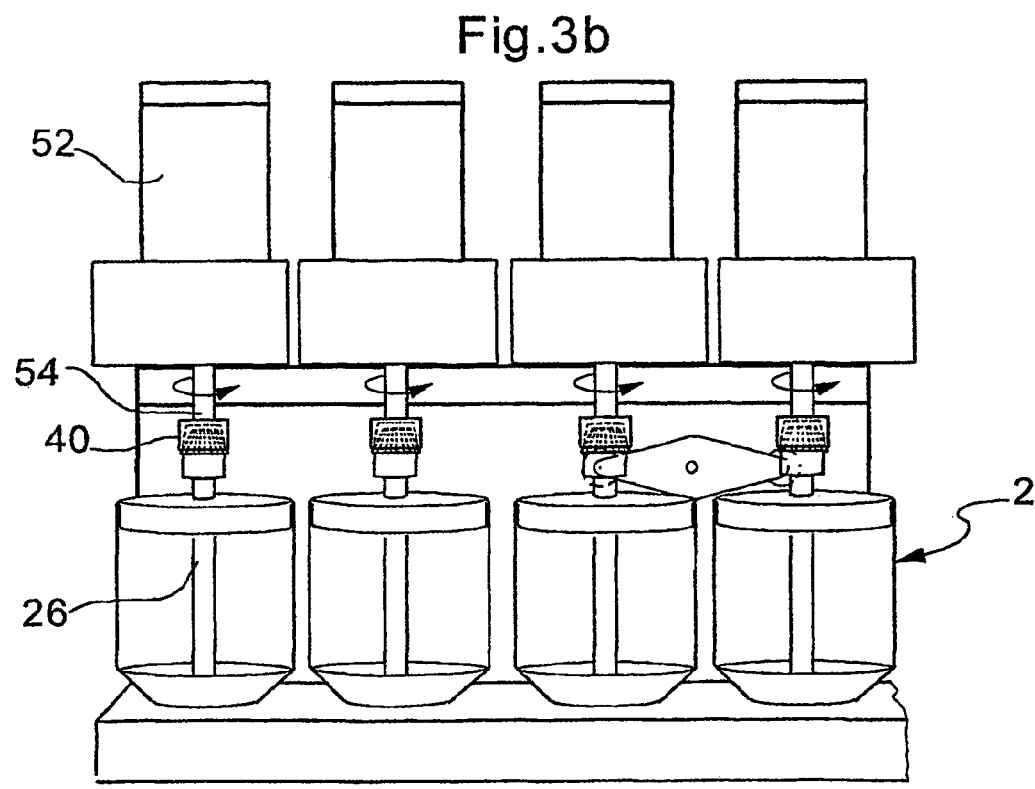
Figure 4:
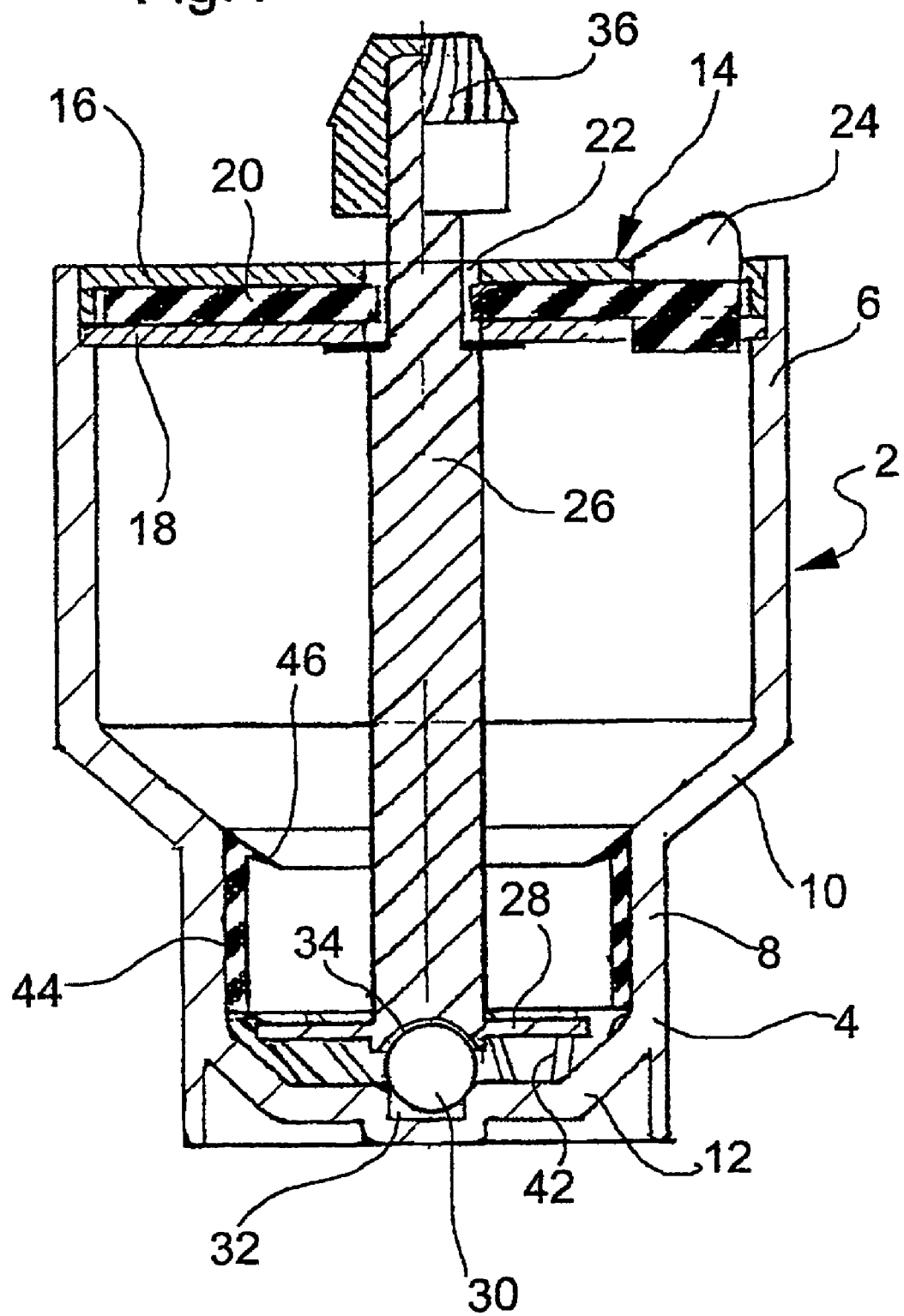
FIG. 4 is a partially sectioned front elevation of an element of FIG. 1.

Equipment for deconstituting samples, as shown in FIGS. 1 to 3, generally includes a deconstitution station, generally indicated 50, which includes motor means 52 with a drive shaft 55, the distal end of which supports a hollow engagement member 40, the internal wall of which is formed for engagement with the element 36 of the deconstitution device. The motor 52 and the shaft associated therewith are movable between a raised, disengaged position (FIG. 3a) and a lowered position (FIG. 3b) engaging the shaft 26 of the deconstituting device.

FIGS. 1 to 3 show a preferred embodiment of the invention, which would work with a plurality of deconstituting devices 2, conveyed to the deconstitution station by a support element 54 housing a plurality of deconstituting devices.

It is clear, of course, that the equipment described can operate with deconstituting devices having a differently configured rotatable shaft, and which do not necessarily conform with the deconstituting device 2 described above.

At the same time, it is clear that the structural principle of the equipment described hereafter is applicable to equipment for treating any number of samples.

The equipment includes a casing 56, possibly with a lid (not shown), which covers the deconstitution station 50. The casing 56 supports internally a first tray 58 and a second tray 60 for conveying the deconstituting devices to and from the deconstitution station 50 respectively.

The support member 54, which consists of an elongate prismatic structure, has a plurality of aligned seats 62 for housing a respective deconstituting device 2. The tray 58 for feeding support elements 54 to the deconstitution station includes a plate 64 and at least one conveyor belt, or preferably a pair of endless conveyor belts 66 and 68, slidably mounted on the plate 64, with motor means 70 for advancing the belts.

Within the scope of the invention, it is clear that other, equivalent conveyor means can be considered. For preference, the plate 64 is pivoted at one end 72 to the fixed structure of the tray 58, with motor means being provided which are operable to cause the plate to move alternately between a lowered position and a raised position. At the end opposite that pivoted on the fixed structure, the plate 64 has an aperture 74 around a fixed support element 76. In its raised position, the surface of the plate 64 is substantially flush with the support element 76, while in its lowered position the support element 76 protrudes through the aperture 74.

The conveyor means for advancing the support elements 54 and their associated cutter devices 2 also includes a worm gear 78 and motor means for rotating it. Each support element 54 includes means (not shown) for engaging the thread of the worm gear so that operation of the latter causes the support element 54 to advance in the direction shown by the arrow F2. At the deconstitution station 50, one or more electric motors 52 are supported by a vertically movable slide member 79, operated by a cam 80.

Motor-controlled unloading means 82 are also associated with the tray 60 for disengaging the support element 54 from the worm gear 78 and conveying it onto the tray 60. These unloading means can include pusher arms, for example, or may be constituted by endless conveyor belts, in a configuration similar to that of the conveyor belts associated with the tray 58.

In operation, the steps of which are shown schematically in FIGS. 2a–2e, an operator positions one or more support elements 54 on the tray 58 with their respective deconstituting devices. When the on-off switch for starting an operating cycle is activated, the motor means cause the plate 64 to rise, so that the end thereof opposite the pivoted end 72 is flush with the support member 76. The conveyor belts 66 and 68 are started so as to advance the support element 54 along the direction indicated by the arrow F1, until the element is resting on the support member 76. Once the support element 54 is in position, resting on the member 76, a switch activates the worm gear 78 which meshes with the engagement means on the support element 54 while, at the same time, the plate 64 is lowered, thereby disengaging the support elements from the conveyor belts. The worm gear 78 causes the support member 54 to advance along the direction of the arrow F2 into a position in which the shafts 26 of the deconstituting devices are aligned with the drive shafts 54 of the four motors 52 of the deconstituting station (FIG. 2b). Once the shafts are aligned, the cam 80 is activated so as to allow the slide 79 to descend until the engagement means 40 are engaged with the engagement element 36 of the deconstituting device (see FIG. 3b).

The motors 52 are set to reach high rotary speeds of around 20,000 RPM. Once alignment is achieved, the electric motors 52 are activated for time periods which vary from about 30 to about 180 seconds, in order completely to deconstitute the samples contained in the deconstituting devices.

At the end of the pre-determined processing time, the cam 80 rotates, thereby raising the slide 79 and moving the shafts of the electric motors so they disengage from the shafts of the deconstituting devices; the worm gear 78 then causes the support element 54 to advance until the next four deconstituting devices are aligned with the four electric motors 52 (FIG. 2c), thus initiating a new cycle, deconstituting the samples contained in these devices. After a programmed period of time (around 30–180 seconds), the slide 79 is raised and the worm gear 78 advances the support element 54 into a predetermined position (FIG. 2d), thereby activating a control device which operates the conveyor belts 66 and 68 to feed a second support element 54 to the deconstitution station.

On exit from the deconstitution station, the support element 54 disengages from the worm gear 78 and is pushed by the unloading means 82 on the tray 60 (see FIG. 2e).

Naturally, the apparatus of the invention could have a control unit for controlling the operation of the motor means which carry out the processing cycle, as well as position sensors or the like which would send the control unit a signal for activating the motor means, in dependence on the position of the support element 54. The equipment would also have safety devices for controlling the operating cycle.

In particular, the control unit could be set to interrupt the operating cycle should it detect any operating problems, such as, for example:
  interrupting the cycle if, after a predetermined time from starting up, the motors which operate the worm gear 78 are not working;
  preventing the operating cycle from starting if the tray 60 is full of support elements 54 which have not been removed by an operator.

In addition, in order to make sure that any interruptions in the power supply do not prevent the samples from being fully deconstituted, the control unit can be set to restart the operating cycle from the beginning in the event of the power supply being interrupted, returning all the deconstituting devices to their rest positions.

Naturally, the principle of the invention remaining unchanged, embodiments and manufacturing details may vary widely from those described and illustrated purely by way of non-limitative example.

What is claimed is:

1. An apparatus for deconstituting biological samples, wherein to apparatus includes:
  at least one support element (54) with a plurality of housings (62);
  at least one deconstituting device (2), which fits in the housings (62), wherein the deconstituting device comprises;
    a cupshaped container (4),
    a shaft (26) mounted for rotation inside the container (4), the shaft having a blade-type deconstituting member (28) on the end inside the container and engagement means (36) on its end outside the container for coupling to motor means, wherein the shaft (26) is supported axially by the bottom (12) of the container on ball coupling means (30, 34) acting as the only anti-friction bearing of the device, the shaft and blade-type deconstituting member being freely rotatable inside the container, when driven by motor means, at a sufficiently high speed;
  a deconstitution station (50) which includes at least one motor (52) with a drive shaft (55) for coupling with the engagements means (36) of the shaft (26) of the deconstituting device, the motor being movable between a position disengaged from and a position engaged with the said shaft (26); and
  conveyor means (66, 68, 78) for conveying the support element (54) to the deconstitution station.

2. An apparatus according to claim 1, wherein the conveyor means include a helical worm gear (78) with motor means for rotating it, and in that the support element (54) includes engagement means for coupling with the worm gear.

3. An apparatus according to claim 1, wherein the conveyor means include a support plate (64) for supporting the support elements (54) and endless conveyor belt means (66, 68) slidably mounted over the support plate and operated by motor means (70), the conveyor means being operable to move the support element (54) into a position engaging a worm gear (78).

4. An apparatus according to claim 3, wherein the belt conveyor means (66, 68) are arranged to advance along a path substantially orthogonal to the axis of the worm gear (78) and the support plate (64) is pivoted by one end (72) onto a fixed support structure so that it can oscillate between a raised position and a lowered position, with the support element (54) carried by the conveyer belt being able, in the raised position, to engage the worm gear (78) and being released from the conveyor means when the plate is in the lowered position.

5. An apparatus according to claim from 1, wherein the at least one motor (52) is mounted on a slide element (79) able to move vertically between a raised free position and a lowered position in which the drive shalt (55) engages the shaft (26) of the deconstituting device, with a cam member (80) provided to control the vertical movement of the slide element.

6. An apparatus according to claim 1, wherein the conveyor means include unloading means (82) for disengaging the support element (54) from a worm gear (78) once the deconstitution process is completed in the deconstitution station.

7. An apparatus for deconstituting biological samples, wherein the apparatus includes:

at least one support element (54) with a plurality of housings (62);

at least one deconstituting device (2), which fits in the housings (62);

a deconstitution station (50) which includes at least one motor (52) with a drive shaft (55) for coupling with the engagements means (36) of the shaft (26) of the deconstituting device, the motor being movable between a position disengaged from and a position engaged with the said shaft (26); and conveyor means (66, 68, 78) for conveying the support element (54) to the deconstitution station;

wherein the deconstituting device comprises:

a cup-shaped container (4), a shaft (26) mounted for rotation inside the container (4), the shaft having a blade-type deconstituting member (28) on the end inside the container and engagement means (36) on its end outside the container for coupling to motor means, wherein the shaft (26) is supported axially by the bottom (12) of the container on ball coupling means (30, 34) acting as the only anti-friction bearing of the device, the shaft and blade-type deconstituting member being freely rotatable inside the container, when driven by motor means, at a sufficiently high speed; and wherein the deconstituting device is disposable.

* * * * *